United States Patent [19]

Rice et al.

[11] Patent Number: 5,360,534
[45] Date of Patent: Nov. 1, 1994

[54] ISOMERIZATION OF SPLIT-FEED BENZENE-CONTAINING PARAFFINIC FEEDSTOCKS

[75] Inventors: Lynn H. Rice, Palatine; James G. Hagen, Rolling Meadows; Brian H. Johnson, Long Grove, all of Ill.

[73] Assignee: UOP, Des Plaines, Ill.

[21] Appl. No.: 65,209

[22] Filed: May 24, 1993

[51] Int. Cl.$^5$ .................. C10G 35/085; C07C 5/22
[52] U.S. Cl. .................... 208/139; 208/145; 585/253
[58] Field of Search .............. 208/139, 145, 66; 585/253, 751, 748

[56] References Cited

U.S. PATENT DOCUMENTS

| | | | |
|---|---|---|---|
| 2,915,571 | 12/1959 | Haensel | 260/683.68 |
| 3,192,286 | 6/1965 | Houston, Jr. et al. | 260/683.73 |
| 3,250,816 | 5/1966 | Waldby | 260/666 |
| 3,277,194 | 10/1966 | Cabbage | 260/666 |
| 3,442,794 | 5/1969 | Van Helden et al. | 208/111 |
| 3,631,117 | 12/1971 | Kovach et al. | 260/666 |
| 3,761,392 | 9/1973 | Pollock | 208/93 |
| 3,836,597 | 9/1974 | Sie et al. | 260/683.65 |
| 4,181,599 | 1/1980 | Miller et al. | 208/79 |
| 4,457,832 | 7/1984 | Robinson | 208/66 |
| 4,839,024 | 6/1989 | Ramage et al. | 208/64 |
| 5,003,118 | 3/1991 | Low et al. | 585/253 |
| 5,146,037 | 9/1992 | Zarchy et al. | 585/751 |

Primary Examiner—Paul Lieberman
Assistant Examiner—Lorna M. Douyon
Attorney, Agent, or Firm—Thomas K. McBride; John G. Tolomei

[57] ABSTRACT

The benzene content in a gasoline pool is reduced by an isomerization process that splits a benzene-containing $C_4$–$C_6$ feedstream between at least two reaction zones and combines the feed fractions with effluent streams. The splitting of the feed stream distributes the heat of reaction over two reactors and lowers the relative exotherm. The lower exotherm for benzene saturation permits higher benzene feeds to be processed without reducing product quality.

17 Claims, 1 Drawing Sheet

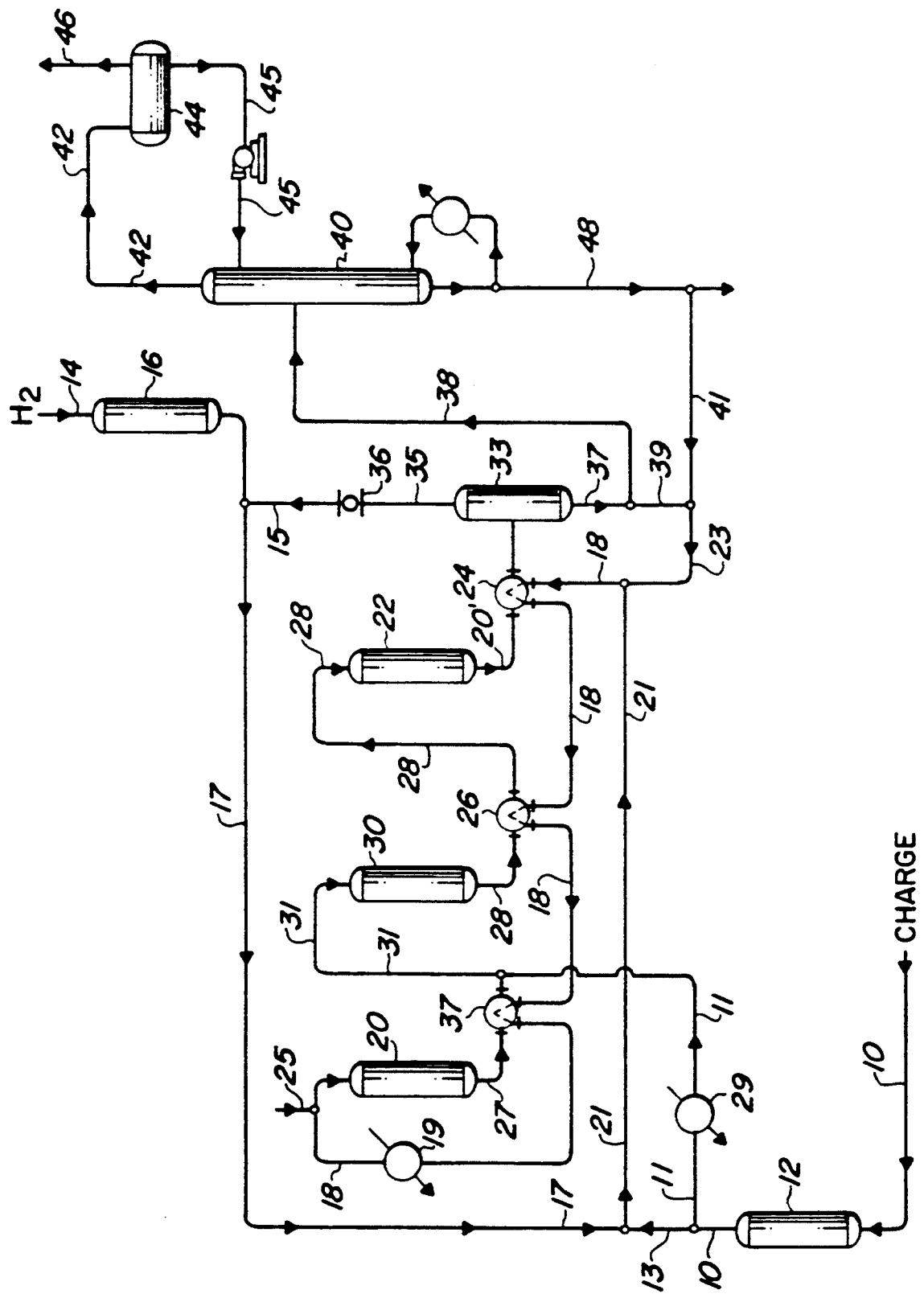

ISOMERIZATION OF SPLIT-FEED BENZENE-CONTAINING PARAFFINIC FEEDSTOCKS

BACKGROUND OF THE INVENTION

This invention relates generally to the isomerization of hydrocarbons. This invention relates more specifically to the processing of benzene-containing hydrocarbon feeds and the isomerization of light paraffins.

DESCRIPTION OF THE PRIOR ART

High octane gasoline is required for modern gasoline engines. Formerly it was common practice to accomplish octane number improvement by the use of various lead-containing additives. As lead is phased out of gasoline for environmental reasons, it is necessary to rearrange the structure of the hydrocarbons used in gasoline blending in order to achieve high octane ratings. Catalytic reforming and catalytic isomerization are two widely used processes for this upgrading.

A gasoline blending pool is usually derived from naphtha feedstocks and includes $C_4$ and heavier hydrocarbons having boiling points of less than 205° C. (400° F.) at atmospheric pressure. This range of hydrocarbon includes $C_4$–$C_9$ paraffins, cycloparaffins and aromatics. Of particular interest have been the $C_5$ and $C_6$ normal paraffins which have relatively low octane numbers. The $C_4$–$C_6$ hydrocarbons have the greatest susceptibility to octane improvement by lead addition and were formerly upgraded in this manner. Octane improvement can. also be obtained by catalytically isomerizing the paraffinic hydrocarbons to rearrange the structure of the paraffinic hydrocarbons into branch-chained paraffins or reforming to convert the $C_6$ and heavier hydrocarbons to aromatic compounds. Normal $C_5$ hydrocarbons are not readily converted into aromatics, therefore, the common practice has been to isomerize these lighter hydrocarbons into corresponding branch-chained isoparaffins. Although the non-cyclic $C_6$ and heavier hydrocarbons can be upgraded into aromatics through dehydrocyclization, the conversion of $C_6$'s to aromatics creates higher density species and increases gas yields with both effects leading to a reduction in liquid volume yields. Therefore, it is preferable to charge the non-cyclic $C_6$ paraffins to an isomerization unit to obtain $C_6$ isoparaffin hydrocarbons. Consequently, octane upgrading commonly uses isomerization to convert normal $C_6$ and lighter boiling hydrocarbons and reforming to convert $C_6$ cycloparaffins and higher boiling hydrocarbons.

In the reforming process, $C_6$ cycloparaffins and other higher boiling cyclic hydrocarbons are converted to benzene and benzene derivatives. Since benzene and these derivatives have a relatively high octane value, the aromatization of these naphthenic hydrocarbons has been the preferred processing route. However, many countries are contemplating or have enacted legislation to restrict the benzene concentration of motor fuels. Therefore, processes are needed for reducing the benzene content of the gasoline pool while maintaining sufficient conversion to satisfy the octane requirements of modern engines.

Combination processes using isomerization and reforming to convert naphtha range feedstocks are well known. U.S. Pat. No. 4,457,832 uses reforming and isomerization in combination to upgrade a naphtha feedstock by first reforming the feedstock, separating a $C_5$–$C_6$ paraffin fraction from the reformate product, isomerizing the $C_5$–$C_6$ fraction to upgrade the octane number of these components and recovering a $C_5$–$C_6$ isomerate liquid which may be blended with the reformate product. U.S. Pat. Nos. 4,181,599 and 3,761,392 show a combination isomerization-reforming process where a full range naphtha boiling feedstock enters a first distillation zone which splits the feedstock into a lighter fraction that enters an isomerization zone and a heavier fraction that is charged as feed to a reforming zone. In both the '392 and '599 patents, reformate from one or more reforming zones undergoes additional separation and conversion, the separation including possible aromatics recovery, which results in additional $C_5$–$C_6$ hydrocarbons being charged to the isomerization zone.

The benzene contribution from the reformate portion of the gasoline pool can be decreased or eliminated by altering the operation of the reforming section. There are a variety of ways in which the operation of the refining section may be altered to reduce the reformate benzene concentration. Changing the cut point of the naphtha feed split between the reforming and isomerization zones from 180° to 200° F. will remove benzene, cyclohexane and methylcyclopentane from the reformer feed. Benzene can alternately also be removed from the reformate product by splitting the reformate into a heavy fraction and a light fraction that contains the majority of the benzene. Practicing either method will put a large quantity of benzene into the feed to the isomerization zone.

The isomerization of paraffins is a reversible reaction which is limited by thermodynamic equilibrium. The basic types of catalyst systems that are used in effecting the reaction are a hydrochloric acid promoted aluminum chloride system and a supported aluminum chloride catalyst. Either catalyst is very reactive and can generate undesirable side reactions such as disproportionation and cracking. These side reactions not only decrease the product yield but can form olefinic fragments that combine with the catalyst and shorten its life. One commonly practiced method of controlling these undesired reactions has been to carry out the reaction in the presence of hydrogen. With the hydrogen that is normally present and the high reactivity of the catalyst, any benzene entering the isomerization zone is quickly hydrogenated. The hydrogenation of benzene in the isomerization zone increases the concentration of naphthenic hydrocarbons in the isomerization zone.

A large percentage of the $C_4$–$C_6$ paraffin fractions that are available as feedstocks for $C_4$–$C_6$ isomerization processes include cyclic hydrocarbons. Cyclic hydrocarbons present in the reaction zone or formed in the reaction zone tend to be absorbed on the isomerization catalysts. Absorption of the cyclic compounds blocks active sites on the catalyst and thereby inhibits the isomerizable paraffins from the catalyst. This exclusion diminishes the overall conversion of the process. As a result, removal of cyclic hydrocarbons from an isomerization process has been generally practiced to increase conversion of the paraffins to more highly branched paraffins. Complete removal of cyclic hydrocarbons by ordinary separation cannot be achieved due to the boiling points of the $C_6$ paraffins and many of the cyclic hydrocarbons, in particular, normal hexane and methylcyclopentane.

It is also known to eliminate cyclic hydrocarbons by opening rings. U.S. Pat. No. 2,915,571 teaches the reduction of naphthenes in an isomerization feed fraction by contact with a ring opening catalyst containing an iron group metal in a first reaction zone, and subsequent isomerization of the feed fraction by contact with a different catalyst in an isomerization zone. Opening of the cyclic hydrocarbons has the two fold advantage of eliminating the cyclic hydrocarbons that can cause catalyst fouling and increasing the volume of lower density isomerizable hydrocarbons that in turn increases product yields. The use of different catalysts for ring opening and isomerization imposes a major drawback on the process of U.S. Pat. No. 2,915,571 since it requires at least one additional reaction zone. U.S. Pat. No. 3,631,117 describes a process for the hydro-isomerization of cyclic hydrocarbons that uses a zeolite supported Group VIII metal as a ring opening catalyst at high severity conditions and as an isomerization catalyst at low severity conditions to obtain cyclic isomers having at least one less carbon atom per ring than the unconverted cyclic hydrocarbons. It is also known from U.S. Pat. No. 4,834,866 that rings can be opened in an isomerization zone using a chlorided platinum alumina catalyst at moderate isomerization conditions. When high severity operating conditions are used to open rings, substantial cracking of $C_4$-$C_6$ hydrocarbons to light ends will also occur. Therefore, high severity conditions to open rings in $C_4$-$C_6$ hydrocarbon feedstocks are usually avoided.

Apart from any problems posed by the saturation of the benzene and the resulting increase in the concentration of cyclic hydrocarbons, the saturation of benzene has the disadvantage of raising the temperature in the isomerization zone. In order to achieve a desired conversion, the feed to the isomerization zone is heated to a temperature that will promote the isomerization reaction. The additional heat resulting from benzene saturation can raise the temperature of the isomerization zone above that which will provide the highest conversion of less highly branched $C_5$ and $C_6$ hydrocarbons to more highly branched $C_5$ and $C_6$ hydrocarbons. It has therefore been difficult to process high concentrations of benzene in feeds to $C_5$ and $C_6$ isomerization zones. The heat associated with benzene saturation has either posed limitations on the amount of benzene that can be processed in an isomerization zone or have reduced yields of desired isomers.

It is, therefore, an object of this invention to provide a process that will facilitate the removal of benzene from the gasoline pool.

It is a further object of this invention to advantageously increase the benzene saturation capacity of a light paraffin isomerization process.

A yet further object of this invention is to reduce the loss of light paraffin conversion from the saturation of benzene in an isomerization process.

BRIEF DESCRIPTION OF THE INVENTION

This invention is a process for isomerizing a feedstock comprising $C_4$-$C_6$ paraffins and benzene by splitting the benzene containing feedstream between at least two reaction zones and combining the feed fractions with the effluent streams of the reaction zones to saturate benzene with isomerization catalyst while maintaining favorable isomerization temperatures in the reaction zones. The benzene content in the gasoline pool is reduced by its saturation in the isomerization process. The splitting of the feed stream distributes the heat of reaction over two reactors and lowers the maximum exotherm selective to that developed in any individual reactor. The lower exotherm permits the saturation of higher benzene content feeds in a multi-reactor isomerization zone without reducing product quality or the reduction of the maximum temperature of any of the reaction zones for a given level of benzene saturation.

The feed splitting aspects of this invention require at least two reaction zones. These reaction zones are operated to accomplish some degree of isomerization along with saturation of benzene. The reaction zones can provide partial or essentially full saturation of benzene. Full saturation of benzene refers to an outlet benzene concentration of less than 0.1 mol % in the effluent stream. The at least two reaction zones are needed to split feed entering the process and to perform benzene saturation in each reaction zone. The process is not limited to the use of only two reaction zones for benzene saturation and the benzene containing feed may be split between any number of reaction zones. Additional reaction zones dedicated principally to isomerization may also be provided. In most arrangements, the process will use two reaction zones between which the entering feed is split and a final reaction zone that receives the effluent from the upstream reaction zones for additional isomerization conversion.

Accordingly in one embodiment this invention is a process for the isomerization of $C_4$-$C_6$ paraffinic feedstock that contains at least 1 wt. % benzene. The process separates the feedstock into at least two portions to provide a first and a second feedstream and contacts the first feedstream, a recycle stream and a hydrogen containing gas stream with an isomerization catalyst at isomerization conditions in a first isomerization reactor and recovers a first isomerization zone effluent. The second feedstream and at least a portion of the first isomerization zone effluent contacts an isomerization catalyst at isomerization conditions in a second isomerization reactor to recover a second isomerization zone effluent. At least a portion of the second effluent stream is recovered as the recycle stream.

In a more specific embodiment this invention is a process for the isomerization of $C_5$-$C_6$ paraffinic feedstocks that contain at least 5 wt. % benzene. The process comprises: separating the feedstock into two aliquot portions comprising a first and a second feedstream; combining a hydrogen-rich gas stream and a recycle stream with the first feedstream to provide a combined feedstream; contacting the combined feedstream with an isomerization catalyst at isomerization conditions in a first isomerization reactor and recovering a first isomerization zone effluent; contacting the second feedstream and the first isomerization zone effluent with an isomerization catalyst at isomerization conditions in a second isomerization zone and recovering a second isomerization zone effluent; contacting the second isomerization zone effluent with an isomerization catalyst at isomerization conditions in a third isomerization reactor and recovering a third isomerization zone effluent; and, separating at least a portion of the third isomerization zone effluent into the recycle stream and a product stream.

Other embodiments, aspects and details of this invention are disclosed in the following detailed description of the invention.

BRIEF DESCRIPTION OF THE DRAWING

The FIGURE shows a preferred arrangement for the process of this invention.

DETAILED DESCRIPTION OF THE INVENTION

A basic arrangement for the processing equipment used in this invention can be readily understood by a review of the flow scheme presented in the FIGURE. The FIGURE and this description make no mention of pumps, compressors, receivers, condensers, reboilers, instruments and other well-known items of processing equipment in order to simplify the explanation of the invention. Looking then at the FIGURE, a feedstream comprising $C_5$ and $C_6$ paraffins along with at least 1 wt. % benzene enter the process through line 10 and pass through a drier 12 that removes water and any other catalyst poisons from the feedstream. Lines 11 and 13 split the dried feedstock into two feedstreams. Make-up hydrogen enters the process through line 14 and a drier 16 for removal of water and, if provided, combines with a hydrogen recycle stream 15. The feedstream of line 13 and the dried hydrogen from a line 17 are combined in a line 21 to form a combined feed. The combined feed receives an additional input of isomerization product recycle from a line 23 which provides the feed to isomerization zone 20 via a line 18. The contents of line 18 are heat exchanged in an exchanger 24 against the contents of line 20' which carries the effluent from a third isomerization reactor 22. The contents of line 18 are further heat exchanged in an exchanger 26 against the contents of a line 28 which carries the effluent from a second isomerization reactor 30. The contents of line 18 may be further heat exchanged against the effluent 27 of the first reaction zone in an exchanger 37. After heating in another exchanger 19 the contents of line 18 enter reactor 20. When using a chloride promoted catalyst, a line 25 injects a chloride-containing compound into line 18. The isomerization reactor 20 performs the first stage of isomerization and saturates benzene in the combined feed. Line 27 carries an effluent, at an elevated temperature relative to the contents of line 23, into admixture with the other feed portion, carried by line 11 to provide a second combined feed taken by line 31. Where necessary, the feed portion of line 11 may be heated in an exchanger 29. Line 31 carries a saturated effluent and the additional feed portion into a second isomerization reactor 30. A second stage of isomerization takes place in reactor 30. Following the second stage of isomerization, line 28 carries the partially cooled isomerization effluent from reactor 30 to reactor 22. After further isomerization in reactor 22, an isomerate product is taken by line 20. In those operations that operate with recycle hydrogen a separator 33 receives the isomerization zone effluent and recovers recycle hydrogen overhead through a line 35 which feeds a compressor 36 for the return of hydrogen to the isomerization reactors via line 15. Bottoms from separator 33 pass to a fractionation column 40 via lines 37 and 38. If desired line 39 may divert a portion of the separated isomerization fraction for supplying recycle to the isomerization zones. Fractionation column 40 removes light gases from the isomerate product which are taken overhead by line 42 and withdrawn from the process through the top of a receiver 44 via line 46. Line 45 provides reflux from receiver 44 back to column 40. The stabilized isomerate product is withdrawn from the bottom of fractionator 40 by line 48. A portion of the stabilized product is taken by a line 41. Line 41 and/or the separated fraction diverted by line 39 supply the recycle that enters the isomerization reactors via lines 23 and 18.

Suitable feedstocks for this invention will include $C_4$ plus hydrocarbons up to an end boiling point of about 250° C. (482° F.). The feedstocks that are used in this invention will typically include hydrocarbon fractions rich in $C_4$–$C_6$ normal paraffins. The term "rich" is defined to mean a stream having more than 50% of the mentioned component. In addition, the feedstock will include significant amounts of benzene. In order to realize the advantages of this invention, the concentration of benzene in the feedstock will at least equal 1 wt. % and will normally be at least 2 wt. %. Preferably, the concentration of benzene will equal at least 5 wt. % and will more preferably be in a range of from 10 to 25 wt. %. The upper limit on the concentration of benzene is dictated by the need to have sufficient paraffinic hydrocarbons present for isomerization and to limit the concentration of benzene. The other feed components will usually comprise $C_5$–$C_6$ cyclic and paraffinic hydrocarbons with normal and isohexane providing most of the paraffinic components.

As hereinafter described in more detail, some of the possible isomerization zone catalysts suitable for use in this invention are highly sensitive to water and other contaminants. In order to keep water content within acceptable levels for such catalysts, all of the isomerization zone feed passes first through a drying zone. The drying zone for this purpose may be of any design that will reduce water content to 0.1 ppm or less. Suitable adsorption processes for this purpose are well known in the art. The isomerization zone catalyst is often sulfur sensitive. Suitable guard beds or adsorptive separation processes may be used to reduce the sulfur concentration of the feedstock. The FIGURE shows the treatment of the feedstock upstream of the hydrogen addition point; however, the feedstock may be treated for any necessary water and contaminant removal at any point upstream of the isomerization catalyst.

A hydrogen stream is combined with the feedstock to provide hydrogen for the hydrogenation and isomerization zones. When the hydrogen is added downstream of the feedstock treating section, the hydrogen stream also undergoes drying or other treatment necessary for the sustained operation of the isomerization zone. The saturation of benzene results in a net consumption of hydrogen. Although hydrogen is not consumed by the isomerization reaction, the isomerization of the light paraffins is usually carried out in the presence of hydrogen. Therefore, the amount of hydrogen added to the feedstock should be sufficient for both the requirements of the hydrogenation zone and the isomerization zone.

The amount of hydrogen admixed with the feedstock varies widely. For the isomerization zones, the amount of hydrogen can vary to produce anywhere from a 0.01 to a 10 hydrogen to hydrocarbon mol ratio in the last isomerization zone effluent. Consumption of hydrogen by saturation increases the required amount of hydrogen admixed with the feedstock. Therefore, hydrogen will usually be mixed with the feedstock in an amount sufficient to create a combined feed having a hydrogen to hydrocarbon ratio of from 0.1 to 5. Lower hydrogen to hydrocarbon ratios in the combined feed are preferred to simplify the system and equipment associated with the addition of hydrogen. At minimum, the hydrogen to hydrocarbon ratio must supply the stoichiometric requirements for the saturation reaction. In order for the saturation to take place at the mild conditions of this invention, it is preferable that an excess of hydrogen be provided with the combined feed. Although no net hydrogen is consumed in the isomerization reaction, the isomerization zone will have a net consumption of hydrogen often referred to as the stoichiometric hydrogen requirement which is associated with the saturation reaction and a number of side reactions that occur. These side reactions include saturation of olefins and aromatics, cracking and disproportionation. Hydrogen in excess of the stoichiometric amounts for the side reactions is maintained in the isomerization zone to provide good stability and conversion by compensating for variations in feedstream compositions that alter the stoichiometric hydrogen requirements and to prolong catalyst life by suppressing side reactions such as cracking and disproportionation. Side reactions left unchecked reduce conversion and lead to the formation of carbonaceous compounds, i.e., coke, that foul the catalyst.

It has been found to be advantageous in some cases to minimize the amount of hydrogen added to the feedstock. When the hydrogen to hydrocarbon ratio at the effluent of the isomerization zone exceeds about 0.1, it is not economically desirable to operate the isomerization process without the recovery and recycle of hydrogen to supply a portion of the hydrogen requirements. Facilities for the recovery of hydrogen from the effluent are needed to prevent the loss of product and feed components that can escape with the flashing of hydrogen from the isomerization zone effluent. These facilities add to the cost of the process and complicate the operation of the process. It is possible to operate the isomerization zone with the effluent hydrogen to hydrocarbon ratio as low as 0.05 without adversely affecting conversion or catalyst stability. Accordingly where possible, the addition of hydrogen to the feedstock will be kept to below an amount that will produce a hydrogen to hydrocarbon ratio in excess of 0.1 and more preferably 0.05 in the effluent from the isomerization zone.

In this invention, split feed and hydrogen enters at least two isomerization zones for the rearrangement of the paraffins contained therein from less highly branched hydrocarbons to more highly branched hydrocarbons. Furthermore, at least two of the isomerization zones saturate the benzene contained in the feed. The isomerization zones use a solid isomerization catalyst to promote the isomerization reaction. The catalyst used in the process can be distributed equally or in varying proportions between the reactors. There are a number of different isomerization catalysts that can be used for this purpose. The two general classes of isomerization catalysts use a noble metal as a catalytic component. This noble metal, usually platinum, is utilized on a chlorided alumina support when incorporated into one general type of catalyst and for the other general type of catalyst the platinum is present on a crystalline alumina silicate support that is typically diluted with an inorganic binder. Preferably, the crystalline alumina type support of the latter catalyst type is a zeolitic support and more preferably a mordenite type zeolite. The zeolitic type isomerization catalysts are well known and are described in detail in U.S. Pat. Nos. 3,442,794 and 3,836,597.

Although either type of catalyst may be used in this invention, the preferred catalyst is a high chloride catalyst on an alumina base that contains platinum. The alumina is preferably an anhydrous gamma-alumina with a high degree of purity. The catalyst may also contain other platinum group metals. The term platinum group metals refers to noble metals excluding silver and gold which are selected from the group consisting of platinum, palladium, germanium, ruthenium, rhodium, osmium, and iridium. These metals demonstrate differences in activity and selectivity such that platinum has now been found to be the most suitable for this process. The catalyst will contain from about 0.1 to 0.25 wt. % of the platinum. Other platinum group metals may be present in a concentration of from 0.1 to 0.25 wt. %. The platinum component may exist within the final catalytic composite as an oxide or halide or as an elemental metal. The presence of the platinum component in its reduced state has been found most suitable for this process.

The catalyst also contains a chloride component. The chloride component termed in the art "a combined chloride" is present in an amount from about 2 to about 10 wt. % based upon the dry support material. The use of chloride in amounts greater than 5 wt. % have been found to be the most beneficial for this process.

There are a variety of ways for preparing the catalytic composite and incorporating the platinum metal and the chloride therein. The method that has shown the best results in this invention prepares the catalyst by impregnating the carrier material through contact with an aqueous solution of a water-soluble decomposable compound of the platinum group metal. For best results, the impregnation is carried out by dipping the carrier material in a solution of chloroplatinic acid. Additional solutions that may be used include ammonium chloroplatinate, bromoplatinic acid or platinum dichloride. Use of the platinum chloride compound serves the dual function of incorporating the platinum component and at least a minor quantity of the chloride into the catalyst. Additional amounts of the chloride must be incorporated into the catalyst by the addition or formation of aluminum chloride to or on the platinum-alumina catalyst base. An alternate method of increasing the chloride concentration in the final catalyst composite is to use an aluminum hydrosol to form the alumina carrier material such that the carrier material also contains at least a portion of the chloride. Halogen may also be added to the carrier material by contacting the calcined carrier material with an aqueous solution of the halogen acid such as hydrogen chloride.

It is generally known that high chlorided platinum-alumina catalysts of this type are highly sensitive to sulfur and oxygen-containing compounds. Therefore, the feedstock must be relatively free of such compounds. A sulfur concentration no greater than 0.5 ppm is generally required. The presence of sulfur in the feedstock serves to temporarily deactivate the catalyst by platinum poisoning. Activity of the catalyst may be restored by hot hydrogen stripping of sulfur from the catalyst composite or by lowering the sulfur concentration in the incoming feed to below 0.5 ppm so that the hydrocarbon will desorb the sulfur that has been adsorbed on the catalyst. Water can act to permanently deactivate the catalyst by removing high activity chloride from the catalyst and replacing it with inactive aluminum hydroxide. Therefore, water, as well as oxygenates, in particular $C_1$–$C_5$ oxygenates, that can decompose to form water, can only be tolerated in very low concentrations. In general, this requires a limitation of oxygenates in the feed to about 0.1 ppm or less. As previously mentioned, the feedstock may be treated by any method that will remove water and sulfur compounds. Sulfur may be removed from the feedstock by hydrotreating. Adsorption processes for the removal of sulfur and water from hydrocarbon streams are also well known to those skilled in the art.

Operation of the reaction zone with a chloride promoted catalyst also requires the presence of a small amount of an organic chloride promoter. The organic chloride promoter serves to maintain a high level of active chloride on the catalyst as small amounts of chloride are continuously stripped off the catalyst by the hydrocarbon feed. The concentration of promoter in the reaction zone is usually maintained at from 30 to 300 ppm. The preferred promoter compound is carbon tetrachloride. Other suitable promoter compounds include oxygen-free decomposable organic chlorides such as perchloroethylene, propyldichloride, butylchloride, and chloroform to name only a few of such compounds. The need to keep the reactants dry is reinforced by the presence of the organic chloride compound which may convert, in part, to hydrogen chloride. As long as the process streams are kept dry, there will be no adverse effect from the presence of small amounts of hydrogen chloride.

Operating conditions within the isomerization zone are selected to maximize the production of isoalkane product from the feed components. Temperatures within the reaction zone will usually range from about 40°–260° C. (105°–500° F.). Lower reaction temperatures are preferred for purposes of isomerization conversion since they favor isoalkanes over normal alkanes in equilibrium mixtures. The isoalkane product recovery can be increased by opening some of the cyclohexane rings produced by the saturation of the benzene. However, if it is desired, maximizing ring opening usually requires temperatures in excess of those that are most favorable from an equilibrium standpoint. For example, when the feed mixture is primarily $C_5$ and $C_6$ alkanes, temperatures in the range of 60°–160° C. are desired from a normal-isoalkane equilibrium standpoint but, in order to achieve significant opening of $C_5$ and $C_6$ cyclic hydrocarbon ring, the preferred temperature range for this invention lies between 100°–200° C. When it is desired to also isomerize significant amounts of $C_4$ hydrocarbons, higher reaction temperatures are required to maintain catalyst activity. Thus, when the feed mixture contains significant portions of $C_4$–$C_6$ alkanes the most suitable operating temperatures for ring opening and isoalkane equilibrium coincide and are in the range from 145°–225° C. The reaction zone may be maintained over a wide range of pressures. Pressure conditions in the isomerization of $C_4$–$C_6$ paraffins range from 7 barsg to 70 barsg. Higher pressures favor ring opening, therefore, the preferred pressures for this process are in the range of from 25 barsg to 60 barsg when ring opening is desired. The feed rate to the reaction zone can also vary over a wide range. These conditions include liquid hourly space velocities ranging from 0.5 to 12 hr.$^{-1}$, however, space velocities between 0.5 and 3 hr.$^{-1}$ are preferred.

The combined feed enters a first isomerization zone for the isomerization of hydrocarbons and the saturation of benzene that operates at isomerization and benzene saturation conditions. In some cases the saturation of benzene will be the primary reaction occurring in the isomerization zone. It is not necessary to operate the first reaction zone to obtain a complete elimination of benzene. In most cases, the process lowers the benzene concentration in the outlet from the first reaction zone to less than 0.1 wt %. The isomerization and saturation reactor will usually operate at a pressure of from 100 to 1000 psig and more typically in a pressure range of from 300 to 500 psig. The initial reactor and any additional reactors usually operate with a liquid hourly space velocity (LHSV) range of from 1 to 8. The amount of benzene saturation performed in the reaction zones is ordinarily maintained at a level that restricts the temperature rise to the reaction zone to less than about 100° F. In order to initiate benzene saturation, the isomerization zone will typically operate at a temperature of at least 180° F. although lower temperatures are also known to provide some benzene saturation. Preferably the first reaction zone will have a maximum outlet temperature of 280° F. In most cases, the reaction zone will operate at inlet temperatures of between 200°–220° F. Such operating temperatures are somewhat lower than typical isomerization temperatures which lie in a range of 260°–340° F. The lower temperatures for the saturation reaction are preferred to avoid unwanted side reactions and to provide a two-phase flow out of the isomerization reactor. The two-phase flow provides additional temperature control to compensate for changes in the benzene feed concentration to the reaction zone. Preferred outlet conditions will limit the vapor fraction to 0.9 or less and usually corresponds to operate with an outlet temperature above 15°–25° F. below the dew point of the effluent.

The amount of benzene saturation and the temperature rise that takes place in the first reactor is a direct result of the initial feed benzene concentration, the split of feed between the reaction zones receiving the initial feed, and the temperature rise in each reaction zone where benzene saturation occurs. The proportion of feed split between the two reaction zones will be determined by the overall benzene concentration and the temperature rise through the reaction zones. The feed split between the reaction zone and the amount of recycle sent back to the reaction zones is generally set to maintain a concentration of 5 wt % benzene when admixed with the recycle liquid.

Typically, a greater proportion of feed is transferred to the second reaction zone. The first reaction zone will usually receive from 25 to 45% of the feedstock. For a feed containing about 15 mol % benzene, from 30–40% of the feed will usually enter the first reaction zone with the remainder sent to a second reaction zone. The amount of recycled effluent entering the first reaction zone can also undergo adjustment to control the temperature rise. The amount of feed recycled to the first and second or any additional reaction zones receiving a split of the initial benzene feed will fall in a range of recycled to combined feed of about 0.5 to 4. Preferably, the ratio of recycle to feed will be in a range of from 1 to 2.5.

The feed to the second reaction zone is a mixture of an aliquot portion of the entering feed and the effluent from the first reaction zone. Operating conditions in the second reaction zone are similar to those for the first reaction zone. However, the operation of the second reaction zone may have slightly elevated temperatures which at the inlet are typically 10°–20° higher than those in the first reaction zone. Preferably the second reaction zone will also have a maximum outlet temperature of 280° F. It is also desirable that the second reaction zone operate in a mixed phase to provide a liquid buffer that controls the temperature rise in the effluent from the reaction zone.

The feed to the first reaction zone undergoes several stages of heat exchange to raise it to operating temperature. The incoming feed may be exchanged against the effluent from each reaction zone, or only heat exchanged against the effluent from the latter reactors which usually tend to operate hotter. A charge heater will typically be provided to the first reaction zone to supply any additional heat required by the first reactor. In processing low benzene concentrations feed with the split feed arrangement, an additional charge heater may be provided for the portion of the split feed that enters subsequent reaction zones. Therefore, the figure shows the optional arrangement of an additional charge heater 29 to heat the split feed portion entering the second reactor.

Operation of the second reaction zone can again achieve either full or partial saturation of the benzene in the combined feed passing therethrough. Whether fully converted or containing benzene, the effluent from the second reaction zone can optionally pass on to a third isomerization zone. In many arrangements, a third and any subsequent isomerization reactors will accomplish a greater portion of the isomerization than either the first or second reaction zone individually and often collectively. The third reaction zone will operate at temperatures in the range of from 200° to 450° F. and preferably in a range of from 260°–400° F. The third reaction zone and any subsequent reaction zones in most instances complete the saturation of benzene. The effluent from the final reaction zone will preferably have a benzene concentration of less than 0.1 wt. %. Additional coolers or exchangers can be provided downstream of the primary benzene separation reactors to cool the subsequent reactors and provide temperatures more favorable for particular isomerization conversions.

Whether operated with two, three or more reaction zones, the effluent of the process will enter separation facilities for the recovery of an isoalkane product. At minimum, the separation facilities divide the reaction zone effluent into a product stream comprising $C_5$ and heavier hydrocarbons and a gas stream which is made up of $C_3$ lighter hydrocarbons and hydrogen. To the extent that $C_4$ hydrocarbons are present, the acceptability of these hydrocarbons in the product stream will depend on the blending characteristics of the desired product, in particular vapor pressure considerations. Consequently, $C_4$ hydrocarbons may be recovered with the heavier isomerization products or withdrawn as part of the overhead or in an independent product stream. Suitable designs for rectification columns and separator vessels to separate the isomerization zone effluent are well known to those skilled in the art.

When hydrogen is received for recycle from the isomerization zone effluent, the separation facilities, in simplified form, can consist of a product separator and a stabilizer. The product separator operates as a simple flash separator that produces a vapor stream rich in hydrogen with the remainder of its volume principally comprising $C_1$ and $C_2$ hydrocarbons. The vapor stream serves primarily as a source of recycle hydrogen which is usually returned directly to the first isomerization reactor. The separator may contain packing or other liquid vapor separation devices to limit the carryover of hydrocarbons. The presence of $C_1$ and $C_2$ hydrocarbons in the vapor stream does not interfere with the isomerization process, therefore, some additional mass flow for these components is accepted in exchange for a simplified column design. The remainder of the isomerization effluent leaves the separator as a liquid which is passed on to a stabilizer, typically a trayed column containing approximately 30 trays. The column will ordinarily contain condensing and reboiler loops for the withdrawal of a light gas stream comprising at least a majority of the remaining $C_3$ hydrocarbons from the feed stream and a liquid bottoms stream comprising $C_5$ and heavier isomerization hydrocarbons. Normally when the isomerization zone contains only a small quantity of $C_4$ hydrocarbons, the $C_4$'s are withdrawn with the light gas stream. After caustic treatment for the removal of chloride compounds, the light gas stream will ordinarily serve as a fuel gas. The stabilizer overhead liquid, which represents the remainder of the isomerization zone effluent passes back to the fractionation zone as recycle input.

The FIGURE show a flow scheme that uses recycle hydrogen. A simplified flow scheme for use without a hydrogen recycle stream would most often take all of the excess hydrogen from the isomerization zone with the overhead stream from the stabilizer drum or receiver. Since, as a precondition for the use of the non hydrogen recycle arrangement, the amount of hydrogen entering the stabilizer is low, the rejection of hydrogen with the fuel gas stream does not significantly increase the loss of product hydrocarbons.

An essential part of this invention is the recycle of a portion of the isomerization zone effluent in combination with the feed to the first reaction zone. The effluent may be taken directly from any of the reaction zones after any desired heat exchange. The bottoms stream from a stabilizer, where provided, may supply the isomerization zone effluent for recycle. As an additional or separate source, the bottoms stream from the separator can supply all or a portion of the isomerization zone effluent recycled to the first reactor. Those skilled in the art will be aware of the most advantageous locations to withdraw the recycle for the first reaction zone to maximize conversion and heat integration aspects of any particular process.

In order to more fully illustrate the process, the following example is presented to demonstrate the operation of the process utilizing the flow scheme of the FIGURE. This example is based in part on a computer simulation of the process and experience with other isomerization and fractionation systems. All of the numbers identifying vessels and lines correspond to those given in the FIGURE.

A $C_5$ plus naphtha feed having the composition given in the Table enters through line 10 and after drying is split to send approximately 37% of the feed to reactor 20 and approximately 63% of the feed to reactor 30. The feed is combined with dry make-up and recycle hydrogen to produce a hydrogen to hydrocarbon ratio of about 2.0 in the feed passing to the first reactor via line 18. Recycle isomerization zone effluent from line 23 combines with the incoming feed at a combined feed ratio of about 1.5 in a pressure of about 500 psig. Exchanger 24 heats the incoming feed and the recycle from a temperature of about 100° F. to a temperature of about 160° F. In the arrangement of this example, the combined feed by-passes exchanger 22 and is heated in exchanger 37 from a temperature of about 160° to a temperature of about 185°. Charge heater 19 raises the temperature of the incoming feed to a temperature of about 190° F. Carbon tetrachloride is added as a chloride promoter at a rate to provide the feedstream entering the first reaction zone with 100 wt. ppm chloride in the incoming feed. After addition of the chloride promoter, the feed contacts a chlorided platinum aluminum catalyst in the first reactor at a liquid hourly space velocity (LHSV) of about 2.0. The effluent from reactor 20 has a temperature of about 250° F. and mixes with the remainder of the reactor charge. Auxiliary charge heater 29 operates without additional heat input and the combined feed enters the second isomerization zone 30 at a combined feed ratio of 1.5 and a temperature of about 205° F. Passage of the second combined feed through the second isomerization zone at a pressure of about 500 psig produces an effluent stream that exits the reactor at a temperature of about 280° and passes to reactor 22 without further heat exchange for additional isomerization. The converted isomerization zone feed leaves reactor 22 at a temperature of about 285° F. which, after heat exchange, is reduced to a temperature of about 260° F. Separator 33 recovers a hydrogen recycle stream that supplies hydrogen to the inlet of reactor 1. In this example, the bottoms from separator 33 provides all of the recycle to the first isomerization zone and the remainder of the separator bottoms enters stabilizer section 40. Stabilizer 40 provides a bottoms product stream having an octane of from 83 to 79 RONC and a mass volume increase of about 3% over the entering feed.

What is claimed is:

1. A process for the isomerization of a $C_4$–$C_6$ paraffinic feedstock that contains at least 1 wt. % benzene, said process comprising:
   a) separating said feedstock into at least two portions comprising $C_6$ hydrocarbons to provide a first and a second feedstream;
   b) contacting said first feedstream, a recycle stream comprising $C_6$ hydrocarbons and a hydrogen containing gas stream with an isomerization catalyst at isomerization conditions in a first isomerization reactor and recovering a first isomerization zone effluent;
   c) contacting said second feedstream and at least a portion of said first isomerization zone effluent comprising $C_6$ hydrocarbons with an isomerization catalyst at isomerization conditions in a second isomerization reactor and recovering a second isomerization zone effluent; and,
   d) recovering at least a portion of said second isomerization zone effluent stream as said recycle stream comprising $C_6$ hydrocarbons.

2. The process of claim 1 wherein said feedstock comprises 5–25 wt. % benzene.

3. The process of claim 1 wherein said hydrogen containing gas stream is mixed with said feedstock to produce a hydrogen to hydrocarbon ratio of less than 0.1 in said isomerization zone effluent stream.

4. The process of claim 1 wherein at least a portion of said second effluent stream contacts an isomerization catalyst at isomerization conditions in a third isomerization reactor and said recycle stream is recovered downstream of said third reactor.

5. The process of claim 1 wherein said first isomerization zone effluent passes to a third reaction zone and said portion of said second isomerization zone effluent is recovered downstream of said third reaction zone.

6. The process of claim 1 wherein the temperature of said first and second effluent streams is less 450° F.

7. The process of claim 1 wherein said feedstock comprises $C_5$–$C_6$ paraffins and cyclic hydrocarbons.

8. The process of claim 1 wherein said hydrogen containing gas stream is admixed with said first feedstream downstream of said separation of said first and second feedstreams from said feedstock.

9. The process of claim 1 wherein said first isomerization effluent has a maximum benzene concentration of 0.1 wt %.

10. The process of claim 1 wherein said first feedstream comprises an aliquot portion of from 25 to 45 vol. % of said feedstock.

11. A process for the isomerization of a $C_5$–$C_6$ paraffinic feedstock that contains at least 5 wt. % benzene, said process comprising:
   a) separating said feedstock into two aliquot portions comprising a first and a second feedstream;
   b) combining a hydrogen-rich gas stream and a recycle stream with said first feedstream to provide a combined feedstream;
   c) contacting said combined feedstream with an isomerization catalyst at isomerization conditions in a first isomerization reactor and recovering a first isomerization zone effluent;
   d) contacting said second feedstream and said first isomerization zone effluent with an isomerization catalyst at isomerization conditions in a second isomerization zone and recovering a second isomerization zone effluent;
   e) contacting said second isomerization zone effluent with an isomerization catalyst at isomerization conditions in a third isomerization reactor and recovering a third isomerization zone effluent; and,
   d) separating at least a portion of said third isomerization zone effluent into said recycle stream and a product stream.

12. The process of claim 11 wherein said feedstock comprises 10–25 wt. % benzene.

13. The process of claim 11 wherein said isomerization catalyst comprises a chlorided platinum catalyst on an alumina support.

14. The process of claim 13 wherein a chloride concentration of from 30–300 ppm is maintained in said isomerization zones by injecting a chloride compound into at least one of said feedstock, feedstreams, and effluent stream.

15. The process of claim 11 wherein said product stream passes to a stabilizer to produce a stabilized product and at least a portion of said stabilized product provides a portion of said recycle stream.

16. The process of claim 11 wherein a separator receives said product stream, said separator recovers a hydrogen containing gas stream and said hydrogen containing gas stream comprises at least a portion of said hydrogen-rich gas stream.

17. The process of claim 11 wherein said first feedstream comprises from 30 to 40% of said feedstock.

* * * * *